United States Patent [19]

Fletcher, III et al.

[11] 4,018,565
[45] Apr. 19, 1977

[54] AUTOMATIC PROCESS TITRATION SYSTEM

[75] Inventors: Kenneth S. Fletcher, III, Norfolk; William E. Earle, North Easton; Jay M. Weiner, Foxboro, all of Mass.

[73] Assignee: The Foxboro Company, Foxboro, Mass.

[22] Filed: Oct. 17, 1975

[21] Appl. No.: 623,381

[52] U.S. Cl. .......................... 23/253 R; 23/230 R; 23/230 A; 23/253 A; 204/1 T; 204/195 T
[51] Int. Cl.² ................. G01N 31/16; G01N 27/44
[58] Field of Search ......... 23/253 A, 253 R, 230 A, 23/230 R, 259; 204/1 T, 195 T

[56] References Cited

UNITED STATES PATENTS

| | | | |
|---|---|---|---|
| 2,977,199 | 3/1961 | Quittner | 23/230 R |
| 2,989,377 | 6/1961 | Leisey | 23/230 R |
| 3,308,041 | 3/1967 | Strickler | 204/1 T |
| 3,625,655 | 12/1971 | Culp, Jr. | 23/253 R |

*Primary Examiner*—R.E. Serwin
*Attorney, Agent, or Firm*—Parmelee, Johnson & Bollinger

[57] ABSTRACT

An automatic titration system and method in which the titrant is generated electrolytically and a two-position slider type ceramic sample valve, reliably, accurately and repetitively obtains a volumetric sample from a process loop and introduces it to a titration cell containing a generator or working compartment and an auxiliary compartment separated by a porous frit. The system also includes a two-position slider type ceramic reagent valve for introducing reagent into the titration cell. Titrant created at a generator electrode surface is dispersed into the bulk of the solution by a magnetically coupled impeller in the working compartment which mixes and also pumps the contents of the cell through the reagent and sample valves in a closed loop. Generator and auxiliary electrodes are connected to a current source which provides the electrolysis current. The progress of the titration is monitored by indicating and reference electrodes in the titration cell connected to an appropriate endpoint indicator, output of which is compared to a known setpoint corresponding to the titration endpoint. The total charge delivered to the generator and auxiliary electrodes during titration is measured by a timer or integrator and read out as a trend output signal. The automatic titration system and method of this invention advantageously lends itself to microprocessor control over the titration reaction and titrator sequencing.

27 Claims, 8 Drawing Figures

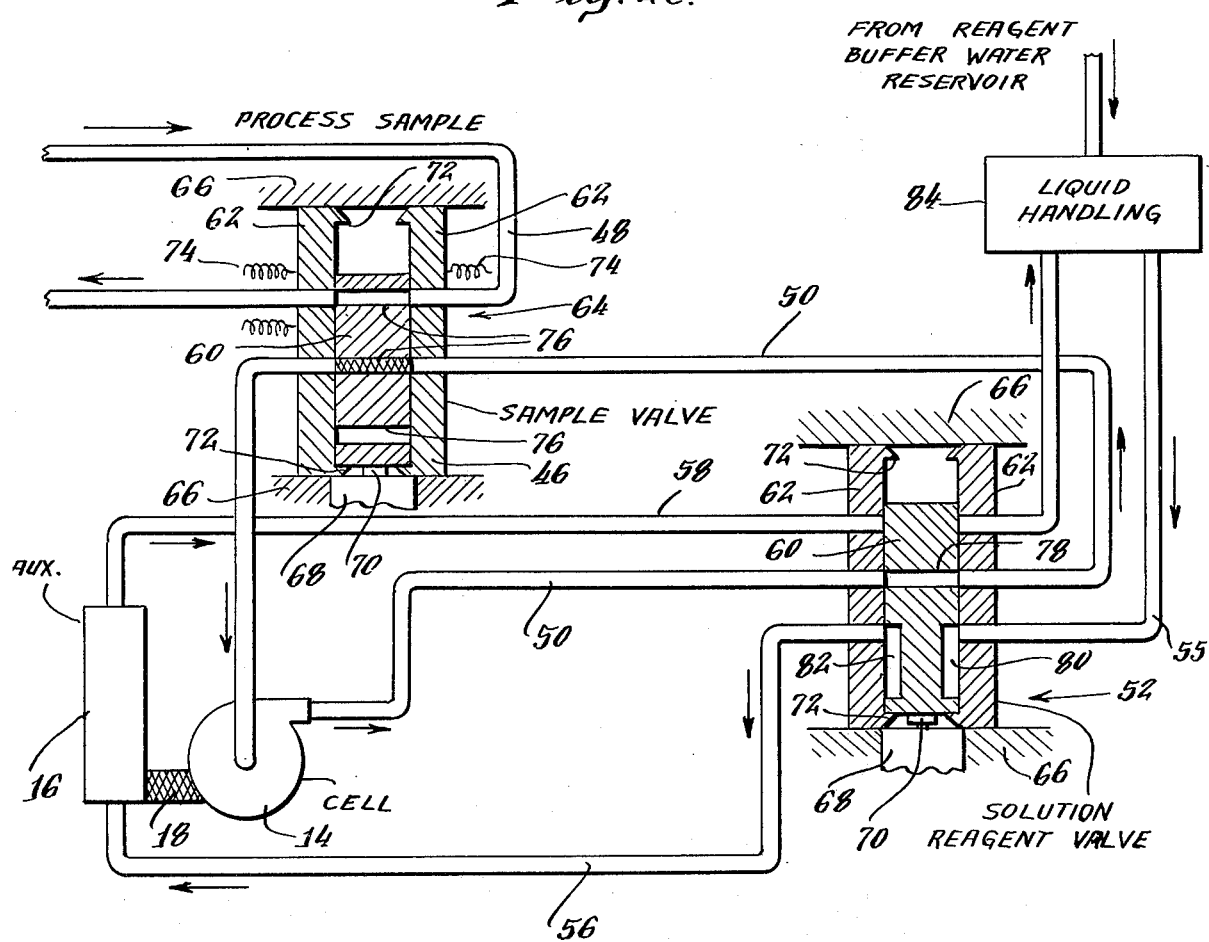

AUTOMATIC PROCESS TITRATION SYSTEM

BACKGROUND OF THE INVENTION

The present invention relates to the field of titration for determining the concentration of an unknown material in a solution by stoichiometric reaction of a known titrant with the unknown titrate and recognition of the endpoint. In a particular aspect, the invention is directed to an automatic titration system and method for use in on-stream process monitoring and control applications. Not only is the system and method for the invention capable of performing routine and repetitive titrations at a faster rate than is presently achieved by semiautomatic or manual methods, but with microprocessor control, according to another aspect of this invention, greater flexibility and reliability with more complex titrations maybe obtained.

In the basic laboratory titration procedure, the titrant is accurately volumetrically added, such as by a buret, to a predetermined volume or weighted portion of the sample unknown to react therewith until the endpoint is reached and observed, usually visually as by an indicator color change. Some attempts at applying automatic titrators in industrial process applications are discussed in "Automatic Titrators", J. P. Phillips, Academic Press, New York, 1959. Many of these attempts have merely involved laboratory techniques through the use of complex mechanical components that record a titration curve, or stop the titration at the endpoint by mechanical or electrical means, instead of by manual attention. These devices and methods are more properly considered semiautomatic where sample preparation, addition of sample to the device, removal of sample, and cleaning of the titration chamber between titrations must be performed manually. Even a continuous titrator utilizing feedback principles through application of a servomechanism requires accurate metering of a portion of the process stream into the reaction or titration chamber together with controlled metering of a titrant reagent in such a manner as to maintain a balanced condition. The large volumes of standard reagent required in these processes necessitate skilled and time consuming manual attention.

The need for preparation of standard solution and the utilization of complex hardware such as volumetric metering pumps and motor driven burets employed in automated volumetric titration techniques may be overcome through the use of coulometric titrant addition wherein the titrant reagent is continuously generated. In such a procedure, the more easily measured and controlled electric current used over a period of time relates to the quantity of, and in essence functions as, the titrant. Nevertheless, since volumetric sampling is still required in such a procedure, automating this technique in the past has involved complex mechanical components involving critical liquid delivery systems and delicate mechanical hardware having small liquid ports, all of which requires high maintenance.

The automatic titration system and method according to the present invention overcomes many of the difficulties encountered with the previous devices and methods for automatic titration and results in advantages not heretofore obtained. The present invention provides an acceptable industrial automatic process titrator capable of continuous unattended operation at the process site and which is easily serviceable due to the elimination of complex precision mechanical components. The automatic titration system of this invention receives samples, performs analyses, and communicates with monitoring or control equipment quickly and reliably so that titrations can be repeated at a high rate of one cycle in approximately 2 minutes. In addition, the automatic titration system and method of this invention advantageously lends itself to microprocessor control over the titration reaction and titrator sequencing in accordance with another specific aspect of the invention.

SUMMARY OF THE INVENTION

The aforementioned difficulties of the prior automatic titration attempts are overcome according to the present invention through the provision of an automatic titration system and method in which the titrant is generated electrolytically and a specially designed sample valve, reliably, accurately and repetitively obtains a volumtric sample from a process loop and introduces it to a specially designed titration cell. The system also includes a specially designed reagent or flush valve for introducing reagent into the titration cell and cell loop for flushing and analysis purposes.

The automatic titration system according to this invention includes a titration cell containing a generator or working compartment and an auxiliary compartment separated by a hydrodynamically impermeable but wettable porous frit. Titrant created at a generator electrode surface in the working compartment is dispersed into the bulk of the solution by flow of solution through the space between the frit and the generator electrode, i.e., the generator-frit spacing. The generator compartment also contains a magnetically coupled impeller which functions to mix and pump the contents of the cell through a reagent and sample valve in a closed loop.

The reagent and sample valves are slider-type ceramic valves having two positions. In one position, the reagent valve closes the loop between the generator compartment and sample valve creating a relatively high speed titration cell flow loop with no dead volume. In its other position, the reagent valve allows reagent to flow from a reagent reservoir, through the reagent valve, into the flow loop and sample valve, into the generator compartment, back into the reagent valve, into the auxiliary compartment, and finally to drain or storage. In this manner complete flushing of both compartments of the titration cell is obtained. In one position, the sample valve has a sample volume element placed in a high speed process sample loop and a second flow-through port in the titration cell loop maintaining the integrity of reagent flow in the cell. To add sample, the sample valve is moved to its other position and a volumetric element of the sample stream is mechanically moved into the cell reagent stream. A third port or passageway in this valve maintains the flow integrity of the process sample line in this second position.

The generator and auxiliary compartments contain generator and auxiliary electrodes connected to a current source which provides the electrolysis current. The progress of the titration reaction, and hence the titration endpoint, is monitored by indicating the reference electrodes which are also contained in the generator or working compartment of the titration cell. These electrodes are connected to an appropriate endpoint indicator and the output therefrom is compared to a known setpoint corresponding to the titration endpoint. The total charge delivered to the generator and auxiliary electrodes during titration is measured by a timer or integrator and read out as a voltage or current as a trend output signal.

Thus, a feature of this invention is the provision of an automatic titration system and method including a sample valve having the capability of reliable, accurate, and repetitive volumetric sampling and utilizing electric current to generate the titrant.

A further feature of this invention is the provision of an automatic titration system and method having a multicompartment titration cell, in which the titrant is coulometrically generated, connected to a closed loop in which are located slider-type reagent and sample valves operable to enable carrying out of the titration operations.

The foregoing features obviate the necessity of preparation, storage, and volumetric dispensing of titrant and consequently reduce both the hardware and manual operations normally associated with so called automatic titrators previously proposed. The precise, yet comparatively trouble free, slider valves enable accurate sampling and efficient flushing of cell contents in short time intervals without appreciable wear or leakage thus increasing reliability and reducing the need for maintenance.

The active elements of the sample and reagent valves comprise very hard, wear and corrosion resistant, ceramic such as high density alumina. Each assembly comprises a slider sandwiched between two stationary blocks of the same material. Leakage is prevented by micropolishing the contacting ceramic surfaces and spring loading the blocks. Each valve slider has two steady state positions with fixed limit stops, thereby eliminating positioning adjustment, and may be solenoid actuated. Therefore, another feature of this invention is the provision of effective, comparatively mechanically simple and trouble free sample and reagent valves for use in an automatic titration system.

While the sequencing of the mechanical and electrical operations of the automatic titration system and method according to this invention may be accomplished with appropriately designed control circuitry, greater flexibility can be obtained by replacement of the electronic hardware with a microprocessor functioning as the state generator. Thus, according to another aspect of this invention, titrator adjustments, such as endpoint setting, may be effected by simple keyboard entries rather than by potentiometric or circuit changes, with all adjustable parameters displayed for operator convenience. With a microprocessor having appropriately developed support capability in the areas of programming, computer simulation and automatic programming of read-only memories, an automatic process titrator with great operational versatility is obtained. Accordingly, a yet another feature of this invention is the provision of a computer based automatic titration system and method for direct control of the titration process, the computer being a dedicated microprocessor designed as an integral part of the system.

The foregoing features, aspects and advantages of the present invention may be better understood from the following description thereof considered together with the accompanying drawings in which:

BRIEF DESCRIPTION OF THE DRAWINGS

FIG. 2 presents a sectional view of the sample and reagent valves according to an embodiment of the present invention in position in the system, illustrating their modes of operation in the sequence of titration; more particularly, FIG. 2B illustrates the valve positions in the pretitrate mode and FIG. 2C illustrates the valve positions in the sample injection and titrate modes;

DESCRIPTION OF THE PREFERRED EMBODIMENTS

Figure 1:
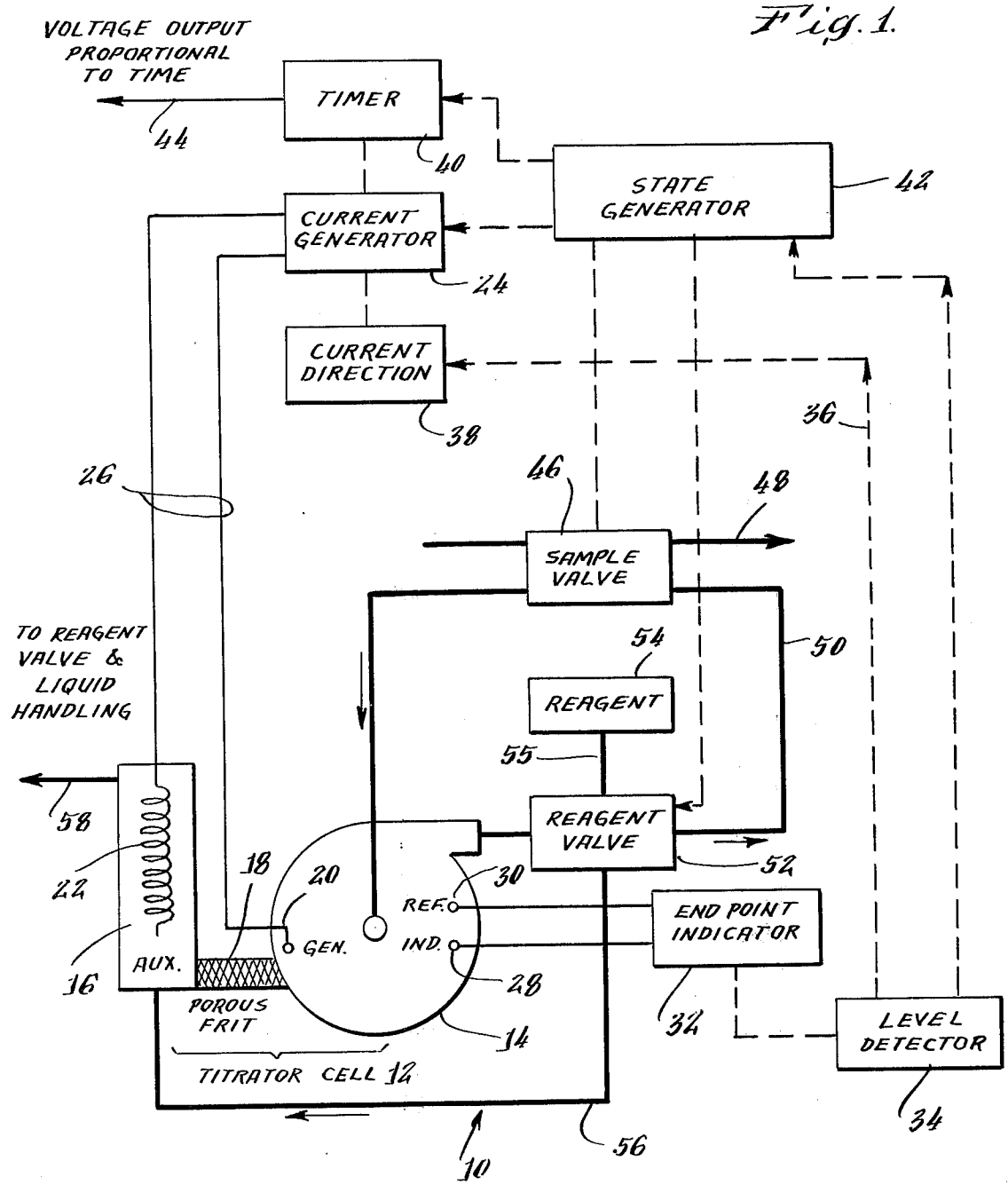
FIG. 1 is a simplified schematic overview of an automatic titration system according to an embodiment of the present invention showing the component parts thereof in block diagram form.

FIG. 1 schematically illustrates, in block diagram form, the automatic titration system 10. The titration cell 12 comprises a generator or working compartment 14, also referred to as a titrating compartment and an auxiliary compartment 16 separated therefrom by a hydrodynamically impermeable but wettable porous frit 18. A generator electrode 20 is positioned in the working compartment 14 in close proximity and parallel to the frit 18 to minimize the electric field in the working compartment. An auxiliary electrode 22 is positioned in the auxiliary compartment 16 and together with the generator electrode 20 is connected to a current source 24 through appropriate leads 26. Titrant is created at the generator electrode surface and rapidly dispersed into the bulk of the solution by flow of solution through the generator-frit spacing.

An indicating electrode 28 and a reference electrode 30 are mounted in the working compartment 14 of the titration cell 12 to monitor the progress of the titration reaction and hence the titration endpoint. As will be explained later in reference to the more detailed discussion of the titration cell, these electrodes are preferably mounted in the working compartment 14 so as to maximize their separation from the electric field at the generator electrode.

The endpoint indicator 32 is of the potentiometric type such as a pH meter. The level detector 34 operates on the output of the endpoint indicator 32 and may be set to stop the titration at any preselected point by dialing the appropriate millivolt level. Therefore, the output of the reference and indicating electrodes is compared to the desired endpoint or setpoint and feedback utilized, by the signal lines 36 and the current direction means 38, so that the applied current may be reduced in a controlled manner as the endpoint is approached.

The endpoint system illustrated is of the potentiometric type utilizing electrodes such as pH electrodes, ion selective electrodes, noble metal electrodes and the like. However, it is to be understood that other endpoint indicators such as those based on amperometric and colorimetric titration are also possible in accordance with certain aspects of the automatic titration system and method of this invention by substituting the potentiometric endpoint system with a potentiostat or a photosensitive detector connected to an appropriate transducer in the cell.

The current generator or source 24 is synchronized to a timer 40 and both are turned on and off by appropriate signals from a state generator 42. The timer 40 is a time to voltage converter and times out the total elapsed time of applied current and reads out this time as a voltage output at the completion of each titration, as represented by the output arrow 44. This trend output may be transferred to a recorder using a data logger to convert the voltage to a format for storage and processing.

A two position sample valve 46 is located in a process sample stream loop 48 and also in a titration cell loop 50. In one position the sample valve 46 permits process stream flow as well as titration cell contents flow therethrough. In another position, a sample volume is injected into the titration cell loop 50 from the process stream 48. A reagent or flush valve 52 introduces fresh reagent from the reagent reservoir 54 to the cell loop 50, through the titration cell 20, back through the reagent valve 52 and through the auxiliary compartment 16 by means of the reagent flushing loop 56. From the auxiliary compartment 16 the reagent may return to a storage or other liquid handling station or to the drain as schematically represented by the indicating arrow 58. In this manner, the titration cell contents are removed and replaced with fresh reagent prior to the addition of sample thereto.

The basic component parts of the automatic titration system 10, namely the titration cell 12, the endpoint indicator 32 and level detector 34, the timer 40, the current generator 24, the sample valve 46 and the reagent valve 52 are all controlled or sequenced through the titration cycle by the state generator 42.

It is to be understood that the foregoing is an overivew of the system with reference to the illustration of FIG. 1 which is schematic only and that more refined details are set forth below with respect to the description of sequence of operation in reference to the other figures. The construction of the sample and reagent valves as well as the operative sequence of the automatic titration system wall be better understood by reference to FIGS. 2A, 2B and 2C illustrating the sequence of events that occur during the titration cycle and showing the operation of the sample and reagent valves therein.

Figure 2A:
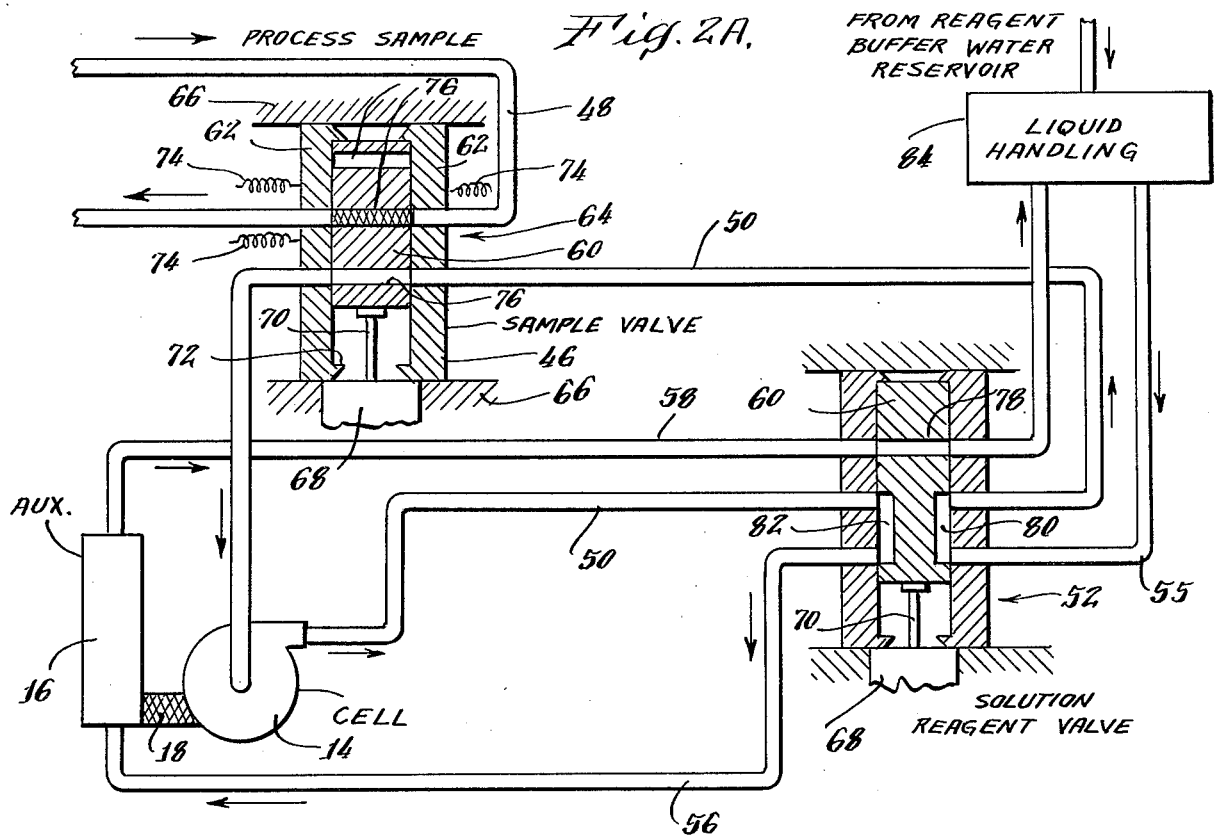
FIG. 2A illustrates the valve positions in reagent flushing mode.
Figure 2B:
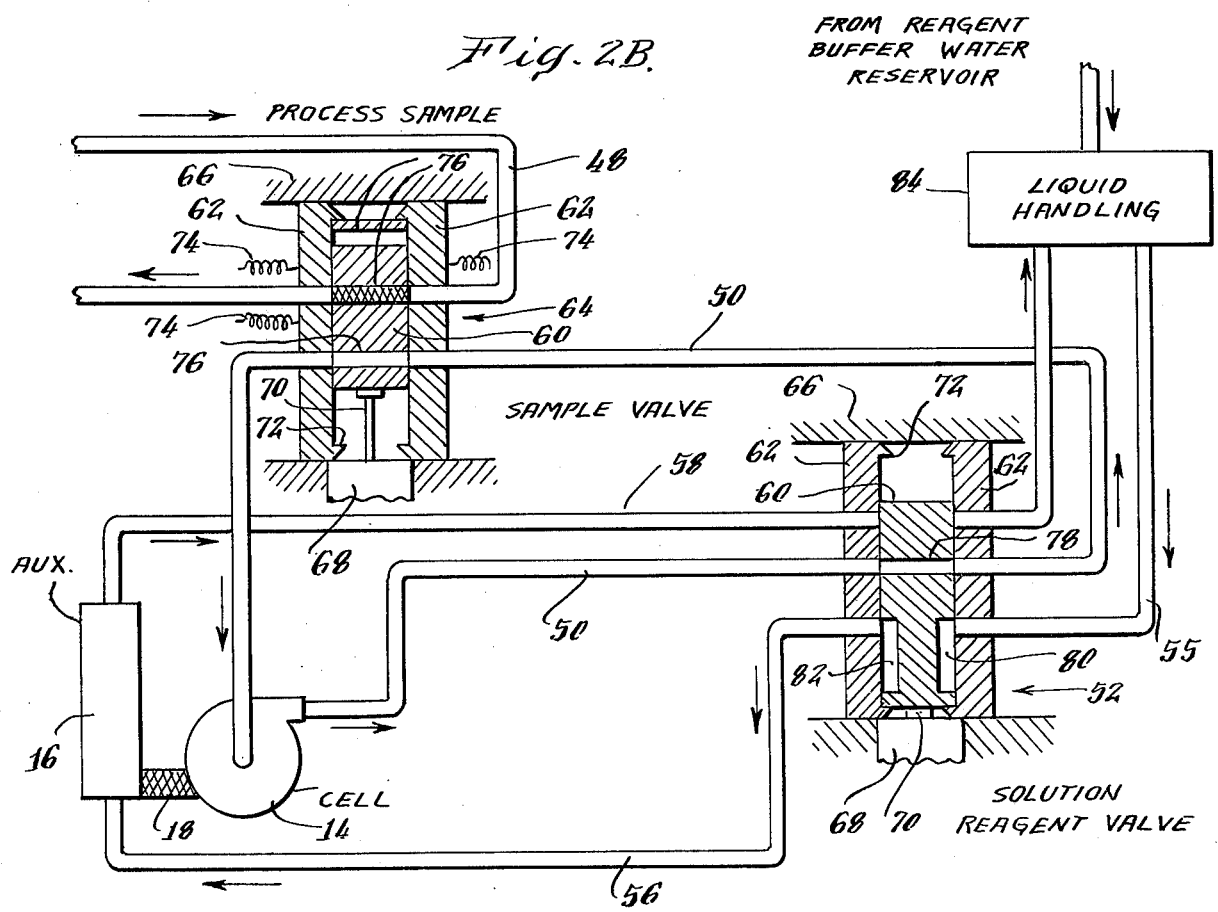

Referring to FIGS. 2A, 2B and 2C, there is shown the sample valve 46 the essential elements of which are a slider 60 sandwhiched between two stationary valve blocks 62 and forming together therewith a valve block assembly 64 as illustrated. The valve block assembly 64 may be mounted in a valve block frame a portion of which is shown at 66 and the remainder of which it being unnecessary to illustrate because it need merely serve to carry the operative parts. The valve block frame 66 also carries solenoids 68 of standard construction having push rods 70 which contact the slider 60 to move it to one of two positions. Although only one such solenoid is illustrated, in FIG. 2B, it is to be understood that each valve includes two such solenoids, see FIG. 3, for activation to two positions. The only active elements in the valve are the solenoids 68 and the slider 60 and at the proper time interval an electric pulse actuates the solenoid to produce sufficient force to switch the valve slider to its opposite position through action of the push rod 70. By establishing fixed limit stops, either through the frame 66 or such as shown at 72, all positioning adjustments are conveniently eliminated. The solenoid push rods 70 may themselves be unanchored to further eliminate any alignment and wear related problems. The valve is fabricated from very hard, wear and corrosion resistant ceramic material such as aluminum oxide. To prevent leakage, the contacting ceramic surfaces may be micropolished and the valve blocks 62 spring loaded, as by spring 74, to hold the assembly together in a tight fit.

Liquid input-output connections may be made to the stationary parts of the valve blocks 62, by means of butt compression elastomeric joints, not shown. The valve blocks 62 contain first and second inlet and outlet means to permit process sample flow through loop 48 through the valve 46 through one inlet and outlet means and cell contents flow through the cell loop 50 through the other inlet and outlet means. The slider 60 has three straight through passageways or openings 76. The sample element is the center hole of the slider 60 and its volume is precisely fixed by the hole diameter and the slider thickness.

Sample from the process stream is introduced into the titration cell 14 by replacing a segment of the cell loop 50 by an equal part of the process stream loop 48 by simply moving the slider 62 containing the passageways 76 for both loops. As shown in FIG. 2A, a continuously flowing sample stream is directed through the sample valve with the slider 62 in one position, shown as "up" in FIG. 2A, and thus the most recent sample may be provided for each titration. To add sample to the cell 14, the slide is moved to its other position, shown as "down" in FIG. 2C, and the volumetric sample is mechanically moved into the cell loop 50. The flow integrity of both the process and cell loop streams is maintained in either position of the slider 60. The advantages of this sample valve are many and varied. Small sample injection ports are not necessary because a segment of the actual flow loop is switched. The sample quantity delivered is inherently repeatable and complicated mechanical hardware such as plungers, mechanical drive mechanisms and fittings are eliminated so that plunger travels, sample delivery overshoots or check valve leakages do not occur. In addition, process compatability with the ceramic material is quite good in most instances.

The reagent or flush valve 52 is similar in construction to the sample valve 46 and like numerals identify like parts thereof. The reagent valve illustrated in FIGS. 2A, 2B and 2C differs from the sample valve in that the valve blocks 62 of the reagent valve 52 contain three inlet and outlet means to permit flow therethrough of the cell loop 50 as well as introduction of reagent to the cell loop from the reagent line 55 and flow from the generator or working compartment 14 to the auxiliary compartment 16 through the reagent flushing loop 56, when used in a flushing mode as will be described hereinafter, and lastly to permit flow from the auxiliary compartment 16 to return to storage or other handling through the return line 58.

The reagent valve slider 60 has a straight through passageway 78 and two edge milled cavities 80 and 82. In one of the reagent slider positions, the down position of FIG. 2B, the straight through passageway 78 permits communication between the inlet and outlet openings in the valve blocks 62 for the cell loop 50 providing a closed loop between the working or generator compartment 14 and the sample valve 46 in which there is high speed flow and no dead volume. In the reagent slider other position, shown as up in FIG. 2A, reagent is allowed to flow from the liquid handling station 84 through the edge milled cavity 80 connecting the inlet and outlet means providing communication between the reagent introduction line 55 and the cell loop 50 so that the reagent flows into the loop 50, the sample valve 46, the working compartment 14, back into the reagent valve 52, and through the edge milled cavity 82 and thence into the auxiliary compartment 16 by means of the reagent flushing loop 56 and finally back to the reagent valve through the auxiliary compartment exit line 58 and thence to the liquid handling station 84 where it may be returned to reagent storage or sent to the drain. In this manner, efficient flushing of all elements of the cell without dead volumes is accomplished quickly. Upon completion of this flush cycle, the reagent slider 60 is switched to its position shown in FIG. 2B closing off the reagent input line 55 and the reagent flushing loop 56 as well as the auxiliary exit line 58.

The liquid handling station 84 is so denominated since it may provide reagent to the system, or, for other flushing or titration purposes, may introduce therein other liquids such as water or buffers through appropriate connection and valving with storage tanks.

A complete titration cycle involves four individual states: flush, zero, sample injection, and titrate. The first three states are preconditions to the fourth which is the actual titration an are representative of the valve positions illustrated in FIGS. 2A, 2B and 2C. These events are controlled by a state generator, or, as described with respect to another embodiment of the automatic titration system below, an electronic processor which produces commands from a time or sensor signal.

FIG. 2A represents the flush state in which both the sample and reagent valves are in their up positions, allowing flushing of the sample injection volume with fresh sample and of the titration cell with fresh reagent, respectively. The zero state is illustrated in FIG. 2B wherein the reagent or flush valve moves to its down position. During this time, the current generator 24, FIG. 1, turns on, and titrates blank reagent to the endpoint level. This, in effect, pretitrates or zeros the reagent, thereby obviating the need for careful and time consuming preparation of reagent. The sample addition and titration state are illustrated in FIG. 2C where it is seen that the sample valve moves to its down position thereby injecting sample into the cell. After sample injection a pH offset occurs and the control system activates the current generator to produce the titrant for neutralizing the offset measurement. (For some measurements, offsets other than pH offsets will be produced—such as colorimetric). The timer 40 is also turned on. The current generator continues until the preselected endpoint valve is obtained at which time the timer output and current can be related to the concentration of the sample.

Thus, in the flushing state, the sample valve center passageway or port is flushed with new sample. Also, the reagent valve opens and the entire titration cell 14 is rinsed with fresh reagent solution. At this time, positive circulation of cell materials may be ceased for a while to permit gases to rise to the top of the cell and be flushed to the drain. The length of time for the flush state is a predetermined value controlled by a built-in clock. The flush state on the reagent valve can be skipped several times, as an option, since the cell contents at completion of a titration are at the endpoint and another sample can be added.

At the completion of the flush state, the flush valve returns to its position shown in FIG. 2B while the sample valve remains in its sample or up position. Switching the flush valve closes the cell to the internal environment and reestablishes the continuous cell flow loop 50.

During the solution zeroing state, the reagent solution pH is adjusted coulometrically to the predetermined endpoint value. Using the pH reference electrodes as sensors, the current generator operates until the desired pH value is reached. Because of the zeroing capability, the automatic titration system does not require an accurately prepared flush solution and the solutions can be reused due to the automatic rezeroing of the cell solution. If the flush state has been skipped under the option described above, the zero state is also eliminated since the cell contents are already at the endpoint level.

As described, sample injection is simply accomplished by switching the straight through passageway through the process sample loop 48 to the cell loop 50. The sample is rapidly mixed into the cell working compartment 14 and an offset signal, i.e. the difference between measured pH and setpoint pH, signals the start of the next titration. In the titration state, the current generator is activated to create titrant until the reacting chemicals return the pH back to a preselected endpoint value. The concentration of the sample may be related to the required time and current and this value processed electronically and the titration cycle repeated again.

Figure 3:
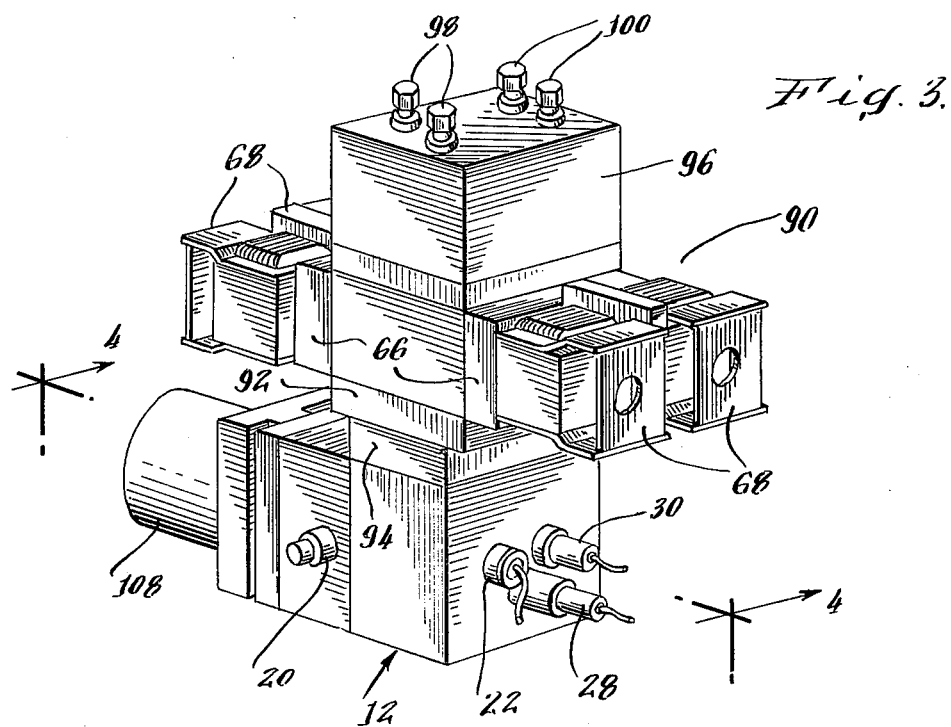
FIG. 3 is a perspective view of the titration cell and sample and reagent valves assembled together in a compact module unit according to an embodiment of the invention.

FIG. 3 shows the overall assembly of the titration system components illustrated in FIGS. 2A, 2B and 2C. Referring to FIG. 3, it is seen that the titration cell 12 and the sample and reagent valves as well as the connections therebetween may be conveniently assembled into a compact modular unit referred to generally as 90. The modular unit 90 includes a center mounting plate 92 to the bottom of which is fastened the titration cell 12 by means of an intermediate connection manifold 94. The valve block frame 66 containing the valve block assemblies, FIGS. 2A, 2B and 2C, is attached to the top of the mounting plate 92. Directly above the valve block assembly is a flow return loop block 96 joined to the top of the valves and containing bored passageways corresponding to the flow lines and loops described in reference to FIGS. 2A, 2B and 2C. The solenoids 68 operate the sample and reagent valves as previously described. The connections 98 and 100 join the modular unit 90 with the process sample stream and the liquid handling station, respectively.

Figure 4:
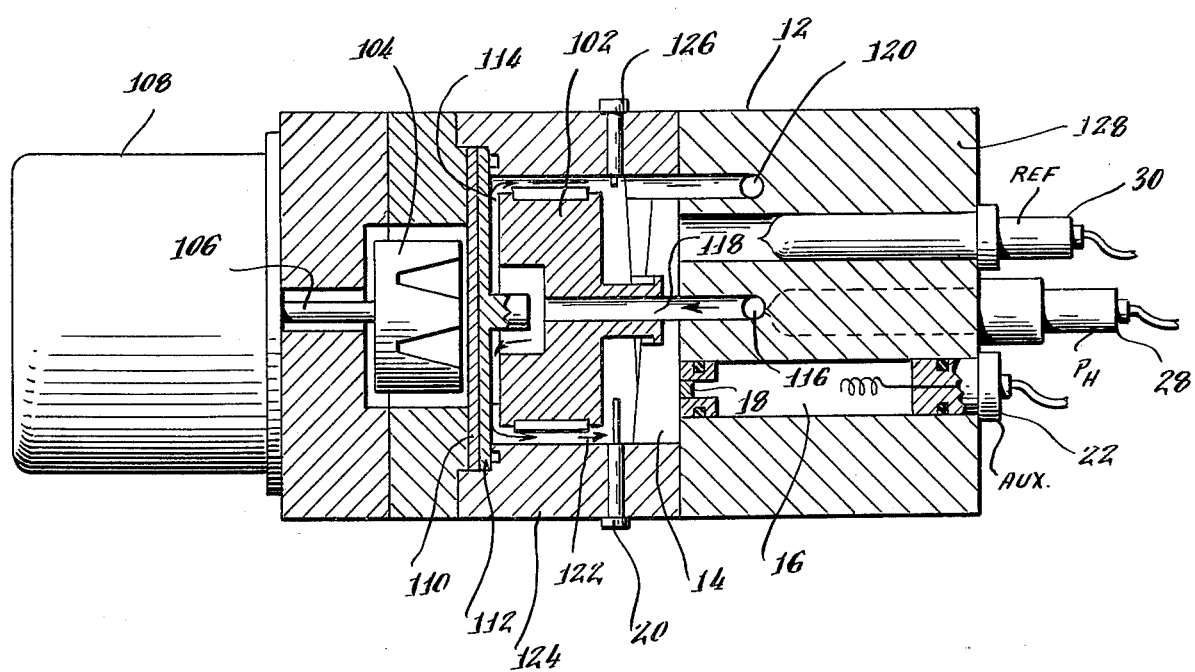
FIG. 4 is a sectional view, taken along the line 4—4 of FIG. 3, showing the interior of the titration cell.

A cross sectional view of the titration cell 12 is seen in FIG. 4. The titration cell 12, includes the generator or working compartment 14 which may be also considered a reaction chamber, and the auxiliary compartment 16. A vaned impeller 102 is located in the generator compartment 14 and functions both as a solution pump and as a chemical mixer. By making the impeller 102 as large as possible in relation to the working compartment 14, the volume of background salt solution is minimized. The impeller is magnetically coupled, through a magnet which may be provided in the impeller by an epoxy potting, to an externally opposite identical magnet 104 attached to the shaft 106 of an AC induction motor 108. A seal is provided between the driving magnet 104 and the compartment 14 by means of a brass backing plate 110 and a bottom plate 112 which may be fabricated of plastic. A bearing washer 114 provides a support for the impeller 102.

The impeller 102 maintains flow through the cell loop 50, FIGS. 1, 2A, 2B and 2C, and carries the injected sample from the sample valve 46 into the titration cell 12. It is desired to maintain as large a flow rate as possible to decrease the time required for mixing and to minimize the response time of this cell by effective mixing of the chemicals electrically generated in the compartment 14. The geometry of the compartment 14 and the impeller 102 are selected to produce uniform chemical distribution. Input to the compartment 14 through the cell loop 50 enters through the opening 116 which is connected to the manifold 94, FIG. 3, and flows down the center opening 118 of the vaned impeller 102 from whence it is circulated around the compartment 14 and through the exit port 120 in the direction shown by the indicating arrows 122.

The liquid exiting the port 120 circulates in the loop 50 and returns down the center of the impeller where it is swept out and up the walls of the compartment 14 with the result that liquid from all regions of the cell is maintained continuously mixed. The auxiliary compartment is connected to exit line 58 by a similar connection, not shown. Also contained in the compartment 14 is the generator electrode 20 mounted in the compartment or wall housing 124 and a temperature compensator 126 mounted in the housing opposite from the generator electrode. A pair of electrodes used for endpoint detection are mounted in the electrode holder 128 which together with the housing 124 defines the working or generator compartment 14. These electrodes are the indicating or pH electrode 28 and the reference electrode 30. The electrode holder compartment 128 also defines the auxiliary compartment 16 in which is mounted the auxiliary electrode 22 and the porous frit or ion transfer membrane 18.

The generator and auxiliary pair of electrodes are separated from each other by the porous frit 18. Since the generator electrode 20 is located directly in the working compartment 14, or reaction chamber, the titrant produced thereby is immediately brought into the chemical reaction. The generator electrode 20 has been positioned directly under the porous frit 18 of the auxiliary compartment 16 so that the electric field produced between the electrodes has a minimum effect on the pH indicating and reference electrodes 28 and 30, respectively.

The auxiliary compartment 16, while closed from the generator compartment 14 by the porous frit 18 and at its top by the auxiliary electrode 22, is open, by means of the exit line 58, FIGS. 1, 2A, 2B and 2C, to the reagent valve 52 for the necessary flushing.

The porous frit 18 must be capable of high ionic transfer, that is, possess low electrical resistance when wetted by the electrolyte solution, but be fairly resistant to bulk solution flow between the compartments 14 and 16. For current to flow through the electrolyte, charge must be transported by ionic motion; thus, when reagent is created at the generator electrode 20, it must be rapidly mixed into the bulk solution so that the background electrolyte, which is present in large excess, may support the required flow of charge through the frit. Fine porosity sintered glass is sufficiently wetted by the reagent solution to give resistance in the range of 50 to 100 ohms and has been satisfactorily employed. Ion exchange membranes may be used for this purpose in certain applications.

The total volume of the titration cell is governed by the degree of dilution that can be tolerated for the desired sensitivity in detecting the equivalence point. Thus, the ratio of volume of sample to the volume contained in the working or generating compartment 14 of the titration cell 12 should be as small as possible. Total cell volume of 30 cubic centimeters has been found satisfactory when utilizing sample valves providing sample injection volumes resulting in dilution factors of 10 to 100. It will be understood that varying ratios can be used depending on the sharpness index, which will decrease with concentration of titrate or unknown sample being analyzed.

The automatic titration system and method of this invention effectively lends itself to microprocessor control allowing real time control over the titration reaction and great flexibility over control of titration sequencing as well as for processing resultant information. Thus, specially designed control circuitry may be replaced by microprocessor software providing operator convenience and generally increased flexibility. For example, all titrator adjustments such as endpoint setting and span may be effected by simple keyboard entries rather than by potentiometric or circuit changes, with adjustable parameters displayed for operator observation.

Figure 5:
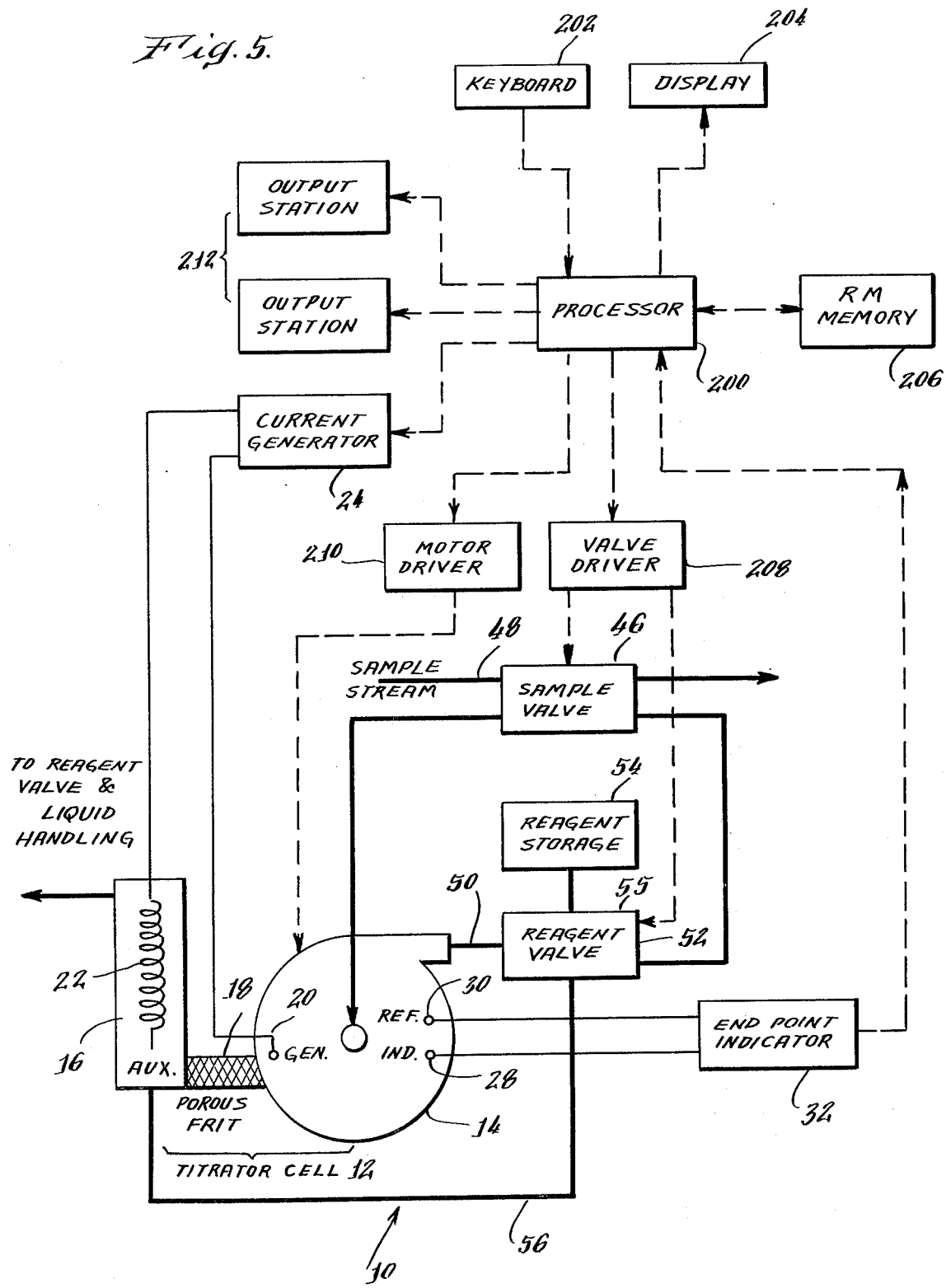
FIG. 5, is a simplified schematic overview, similar to that of FIG. 1, of an automatic titration system showing the use of a microprocessor as a state generator according to an embodiment of this invention.

FIG. 5 illustrates, in schematic form similar to FIG. 1, a microprocessor controlled automatic process titration system and method according to another embodiment of this invention. Referring to FIG. 5, where like parts of FIG. 1 are indicated by like numerals, a microprocessor 200 controls the titration system, hereinafter referred to as the titrator. From the operator's standpoint, the system and method is controlled via the keyboard 202 in conjunction with the display 204. The keyboard 202 may comprise 14 active key switches plus an on/off slide switch. Thus, in addition to the decimal digits zero through nine plus the decimal point, there are three command keys lettered D, F and CL, designating data entry, function select and clear, respectively.

The display 204 comprises two groups of indicators, one of two digits and the other of four digits. The two digit group indicates the current mode of operation while the four digit group of indicators is utilized for display and entry of data.

To select a particular function, the four digit display is cleared by depressing the clear key, the appropriate two digit function code is entered and the function key F is pushed. The specified function code will then appear in the two digit function display and relevant data will appear in the four digit display. Some 15 functions may be selected via the keys. The four functions 00, 10, 20 and 12 are designated control functions, since they enable and disable titrator sequencing, whereas the other functions are for display and modification of parameters. When any of these four functions is entered, the data display indicates pH. Function 00 is unique in that it not only stops normal sequencing of the titrator, but also flushes reagent through the cell for a designated time. By use of this function, a pH buffer solution may be flowed into the cell allowing for standardization of the pH measuring system when required.

The data functions are used to display and modify titration parameters. To modify the data displayed, the titrator must first be stopped by entering the function OO and then any value of the data functions may be altered by clearing the display, entering the new value, and pushing the data enter button. The function codes are as follows:

- 30—Display Endpoint Delay: The endpoint delay is the number of seconds that the titrator waits after doing a zeroing or titrating operation before entering the succeeding state. This delay must be used to allow sufficient time to elapse to ensure that the specified endpoint has actually been reached when slow titration reactions are used.
- 40—Display Time Between Repeats: Time between repeats refers to the waiting interval between successive titration cycles.
- 50—Display pH: This function displays measured pH. Entering a pH value under this function changes the calibration such that the measured pH at the time of entry is identical to the entered pH.
- 61—Display Maximum Current No. 1: The maximum current is the initial current per pH unit of deviation from the end point pH at the start of a zeroing or titrating state. Process No. 1 is a first titration.
- 62—Display Maximum Current No. 2: Same as 61 but for Process No. 2, a second titration.
- 71—Display Setpoint No. 1: The setpoint or endpoint is the desired pH valve at the completion of a zeroing or titrating state.
- 72—Display Setpoint No. 2: Same as 71 but for Process No. 2.
- 81—Display Output Span No. 1: This is the span of output No. 1 in ppm.
- 82—Display Output Span No. 2: Same as 81 but for Process No. 2.
- 91—Display Output No. 1: This merely allows a digital readout of the analog value from output No. 1 in ppm.
- 92—Display Output No. 2: Same as 91 but for Process No. 2.

Figure 6:
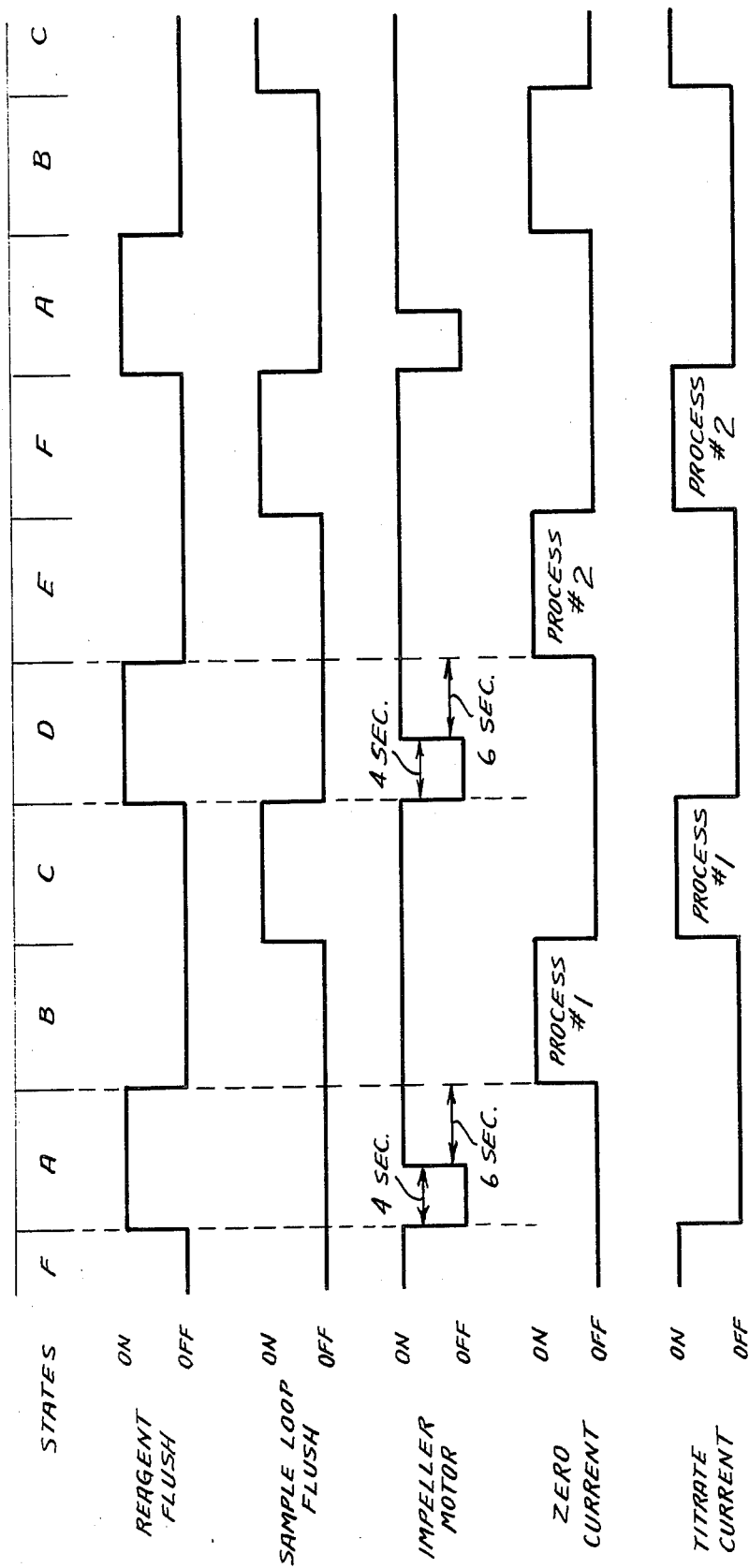
FIG. 6 illustrates the relationship between the various states existing in the operational sequence of the automatic titration system and method.

When the automatic titration systen is performing its operational sequences, the function display 204 blinks the current state of the titration. Three possible states exist as shown in FIGS. 2A, 2B and 2C. In the first state, termed state A, the cell is flushed for a short time interval. In state B, current is turned on to pretitrate the reagent to the pH value selected for setpoint 1. A sample is then injected and state C is entered. In state C the current is turned on until the pH of the reagent plus sample is returned to setpoint 1, completing the first titration. A second titration to setpoint 2 may be performed by an identical sequence of states termed D, E and F. The coulombs required during state C are simply related to the concentration of the unknown, and this concentration is calculated and output as a trend signal with updating after each state C. For two titrations, processes 1 and 2, a second trend output results after each state F. The relationship between the states and the operation of the titrator is illustrated in FIG. 6. Except for states A and D, the titrator states vary in time duration as functions of reagent and sample concentration. Thus, if only the first titration is being performed, process number 1, then the state sequence is ABCABC . . . rather than ABCDEFABCDEF . . . when both titrations are being performed. For titration of process number 2 only, the state sequence is DEFDEF . . .

When the titrator is operating, the function display blinks the current state of the titrator at a once-per-second rate. For example, if the titrator function is 61 and the titrator is running at state D, then once each second the 61 will be briefly replaced with the letters DD. If the titrator is stopped, both processes 1 and 2 off, this fact will be evidenced by the lack of blinking of the function code.

A microprocessor which has been found satisfactory for effective operation of the automatic titration system is an eight bit Intel 8008. The program controlling the titrator may comprise approximately 3500 bytes of fixed code stored in read-only memory (ROM). A small 256 byte read-write memory is used as a temporary storage area for intermediate calculations. The need for variable but nonvolatile parameter storage is filled by a 32 byte read-mostly memory 206, a specially fabricated semiconductor memory whose contents are not volatile with loss of supply power, yet may be electrically altered by an appropriate programming procedure. Operator entered parameter data, such as the endpoint pH and calibration information, are stored in the read-mostly memory 206. The microprocessor, along with its ROM and read-write memory, is assembled as a single circuit board.

There are eight input-output or peripheral devices serviced by the microprocessor 200 shown in FIG. 5. The devices providing input signals to the microprocessor are the keyboard 202, the read-mostly memory 206, and the pH or endpoint indicator 32. Devices directly controlled by the microprocessor 200 are the display 204, the read-mostly memory 206, the valve drivers 208 for the solenoid driven sample valve 46 and reagent valve 52, the motor driver 210 for the titration cell impeller, the coulometric current generator 24, and the two analog output generators 212. In the titrator, as in most computer based instruments, the physical size of the microprocessor 200 is relatively small compared to the physical size of the peripheral equipment which it controls.

A microprocessor program for controlling the titrator is divided into four main sections. First is the background program, a low priority program being executed when time dependent calculations are not involved. The background loop program performs such functions as updating the operator display and checking the keyboard for entries, both of which are relatively noncritical in terms of timing.

The control section of the program is the section that causes the titrator to perform the operational sequences. Although the control program does not itself perform timing, it initiates the various timed intervals needed in the course of a titration and is responsible for operating the solenoid driven valves, controlling the titrating current and performing the coulometric integration.

All timing for the titrator is derived from a 60 Hz clock interrupt, giving a basic time resolution for all timed functions of 16 milliseconds. Multiples of this basic time interval are used by the program to implement the longer time intervals needed for titrator sequencing. Every 16 milliseconds an interrupt program is activated by an external clock signal. This program is used primarily for interval timing under the supervision of the control program. It also monitors the power status, deciding when the restart procedure must be initiated because of a power failure. Power failure protection with automatic restart is built into the microprocessor program so that the titrator is able to restart itself without operator intervention when power is restored after a shutdown. Upon power restoration, the program completely restarts the titration sequence, thereby avoiding the problems associated with attempting to resume a titration interrupted in mid-sequence. Since the control program is designed as an interrupt-activated program, the interrupt program itself is equivalent to a second level of interrupt when the interrupt occurs during control program execution.

Subroutines constitute the fourth main section of the program and, although there are many, the major subroutines in the titrator system are the floating point arithmetic subroutines, the display subroutine, and the read-mostly-memory subroutine. Data in the floating point system used by the titrator consists of three bytes, 16 bits of mantissa and 8 bits of exponent, more than adequate for the resolution and range requirements of the titrator signals. The display subroutine provides the binary-to-decimal conversion of data for output to the numeric operator display. To accommodate the wide range of possible displayed data, the display subroutine provides for the output of a floating decimal point along with the decimal digits. The read-mostly-memory subroutine was required because of the complex read-write procedures.

The program controlled microprocessor not only provides the computational ability and timing needed by the titrator, but also flexibility for modifications in the overall operation of the titration system. Thus, titrating current can be made to follow relationships other than linear and program changes can make scale factors for output concentration available as keyboard entries rather than being built into the program. In addition, although in amperometric and photometric titrations with sharply changing titration curves the endpoint indicator fails to make measuremtn of the progress of the titration reaction prior to the endpoint, thus making direct feedback control of the coulometric current level impossibel, control can nevertheless be obtained by utilizing the storage capacity of the microprocessor. Thus, the initial titration may be performed rapidly with relatively large current according to preestablished instructions and the coulombs of charge required stored. In the succeeding titration, the current is then reduced after some preselected fraction of the total anticipated charge has been applied. After accurate detection of the endpoint, the new titration result is stored and the procedure repeats, thus assuring both accuracy and speed.

Most titrations commonly performed in the analytical laboratory can be performed using the automatic process titration system and method according to this invention. The frequently performed single endpoint acidbase titration is handled extremely well by the titrator with an overall precision and accuracy of ± 0.2%. In addition to strong and weak acid-base titrations, the program logic can be modified to yield information on multi-endpoint systems. Thus, consecutive endpoint titrations such as the alkalinity of natural waters, imparted by a bicarbonate, carbonate and hydroxide and usually determined by titration with acid to the successive carbonate and bicarbonate endpoints, may be performed adequately with agreement within ± 0.5% with this invention. Double endpoint titrations and redox titrations may also be accomplished. The latter simply by replacement of the pH glass electrode with a platinum or other suitable noble metal electrode. In addition to direct titration procedures, it is possible to perform indirect procedures by simple changes in program logic so that slow reactions and back titration procedures may be used as in titrations for metal ions and water hardness.

We claim:

1. An automatic process titration system for measuring the concentration of a process stream comprising:
   a titration cell having two compartments separated by a porous membrane,
   one of the titration cell compartments being a working compartment including an electrode means for generating titrant electrolytically,
   means for detecting a titration endpoint operatively associated with the working compartment,
   the other of the compartments being an auxiliary compartment including an electrode coupled to the generating electrode means for enabling the electrogeneration of titrant,
   positionable sample valve means for obtaining a sample of the process stream,
   the sample valve means having at least two operative positions and being located in relation to the process stream so as to permit process stream flow therethrough in one position and injection of a predetermined amount of sample from the process stream into the titration cell in its other position,
   positionable reagent valve means for introducing reagent for generating titrant to the titration cell,
   the reagent valve means having at least two operative positions and being located in relation to the titration cell so as to permit working compartment contents flow therethrough in one position and introduction of reagent to the titration cell in its other position,
   the sample valve means, reagent valve means and titration cell being interconnected to form a cell loop means for the flow of titration constituents therethrough,
   current source means for providing current to the titrant generating electrodes,
   fluid circulating means for circulating titration constituents,
   valve operating means for positioning the sample and reagent valve means, and
   state generator means operatively connected to the current source means, and to the valve operating means for actuating them in a preset sequence for achieving a titration cycle.

2. An automatic process titration system as claimed in claim 1 wherein the sample and reagent valve means each comprise a two-position slider movably sandwiched between two blocks forming the valve housing, the sliders being activated in a push-pull arrangement.

3. An automatic process titration system as claimed in claim 1 wherein the sample valve means comprises:
   a slider positioned between two valve housing elements and reciprocably movable parallel relative thereto to at least two operative positions,
   the valve housing elements having first inlet and outlet means and second inlet and outlet means,
   the valve slider having at least three passageways located therein so that in either of two operative positions two of the passageways provide communication between the first and second inlet and outlet means, the slider being positionable so that in one position one of the passageways provides communication with the first inlet and outlet means and in the other position the same passageway provides communication between the second inlet and outlet means, and one of the inlet and outlet means is connected to the process stream and the other inlet and outlet means is connected to the cell loop.

4. An automatic process titration system as claimed in claim 1 wherein the reagent valve means comprises:

a slider positioned between two valve housing elements and reciprocably movable parallel relative thereto to at least two operative positions, the valve housing elements having first and second inlet and outlet means, the slider having at least two passageways located therein so that in either of two operative positions the passageway provides communication between one of the inlet and outlet means, one of the inlet and outlet means being connected to the titration cell and the sample valve providing flow therethrough and through the cell loop, the other inlet and outlet means being connected to the cell loop and to a source of reagent to provide flow of reagent through the titration cell, the sample valve means and the cell loop.

5. An automatic process titration system as claimed in claim 4 wherein:

the valve housing elements have first, second and third inlet and outlet means, the slider has at least three passageways located therein so that in either of two operating positions the passageways provide communication between either all or only one of the inlet and outlet means, one of the inlet and outlet means being connected to the auxiliary compartment and permitting flow therefrom when the slider is in its one position aligning one of the passageways for communication therebetween, another of the inlet and outlet means being connected to provide communication between the working compartment and the auxiliary compartment when the slider is in its one position aligning another of the passageways for communication therebetween, the other of the inlet and outlet means being connected to provide communication between a source of reagent and the working compartment when the slider is in its one position aligning the other of the passageways for communication therebetween, one of the inlet and outlet means providing communication between the working compartment and the sample valve when the slider is in its other position with one of the passageways being aligned for communication therebetween, and the other inlet and outlet means being effectively blocked when the slider is in its other position.

6. An automatic process titration system as claimed in claim 5 wherein:

one of the passageways in the slider is a straight-through opening and the other passageways comprise edge milled cavities providing communication between inlet and outlet means located on the same side of the valve housing.

7. An automatic process titration system as claimed in claim 2 wherein the contacting valve elements are formed of micropolished, wear and corrosion resistant ceramic.

8. An automatic process titration system as claimed in claim 1 wherein the means for detecting a titration endpoint comprise an indicating electrode and a reference electrode mounted in the titration cell working compartment and connected to a potentiometric indicating means.

9. An automatic process titration system as claimed in claim 1 wherein the state generator means comprises a microprocessor means for controlling the titration sequence.

10. An automatic process titration system as claimed in claim 1 wherein the fluid circulating means comprises an impeller located in the working compartment of the titration cell and magnetically coupled to an external driver.

11. A modular automatic process titrator comprising:

a titration cell containing electrode means for generating titrant and means for detecting a titration endpoint, a valve block enclosing a positionable sample valve means for obtaining a sample of process stream and introducing it to the titration cell and a positionable reagent valve means for introducing reagent for generatsing titrant to the titration cell, manifold means connecting the valve block and titration cell for providing communication between the sample and reagent valve means and the titration cell, and flow loop block means containing passageways connecting a process sample stream with the sample valve means and providing interconnection between the sample valve means and the reagent valve means and between the reagent valve means and a reagent source.

12. A modular automatic process titrator as claimed in claim 11 wherein:

the sample valve means has at least two operative positions and is located in relation to the process sample stream so as to permit process sample stream flow therethrough in one position and injection of a predetermined amount of sample from the process sample stream into the titration cell in its other position, and the reagent valve means has at least two operative positions and is located in relation to the titration cell so as to permit cell contents flow therethrough in one position and introduction of reagent to the cell in its other position.

13. A modular automatic process titrator as claimed in claim 12 further comprising solenoid valve operating means for positioning the sample and reagent valve means.

14. A modular automatic process titrator as claimed in claim 12 wherein:

the titration cell has two compartments separated by a porous membrane, one of the titration cell compartments being a working compartment including an electrode means for generating titrant electrolytically, the other of the compartments being an auxiliary compartment including an electrode coupled to the generating electrode means for enabling the electrogeneration of titrant, and means for detecting a titration endpoint positioned in the working compartment.

15. A modular automatic process titrator as claimed in claim 14 further comprising impeller means for circulating titration cell contents mounted in the cell worksing compartment and magnetically coupled to an external driver.

16. A microprocessor controlled automatic process titration system for measuring the concentration of a process stream comprising:
a titration cell containing electrode means for generating titrant and means for detecting a titration endpoint,
a current generating means for generating current for the electrode means,
an endpoint indicating means operatively associated with the titration endpoint detecting means and capable of sending a signal in response thereto,
a sample valve drive means for positioning a sample valve means for obtaining a sample of the process stream and introducing it to the titration cell,
a reagent valve drive means for positioning a reagent valve means for introducing reagent for generating titrant to the titration cell, and
microprocessor means for controlling the titration sequence in the system, the microprocessor means being connected to the endpoint indicator for receiving a signal therefrom and including means for relating the endpoint signal to a predetermined setpoint and controlling the current generating means to provide current in response thereto, and
sending actuating signals to the sample and reagent valve drive means in response thereto.

17. A microprocessor controlled automatic process titration system as claimed in claim 16 further including driver means for operating circulation means for circulating titration cell contents and the microprocessor includes means for sending actuating signals to the driver in response to preset programmed conditions.

18. A microprocessor controlled automatic process titration system as claimed in claim 16 wherein the microprocessor means is connected to a keyboard and display for operator input and observation and includes means for providing output to analog generating means.

19. A microprocessor controlled automatic process titration system as claimed in claim 16 wherein the microprocessor means comprises a read-only memory, read-write memory and a read-mostly memory.

20. A method of automatic process titration in which the titrant is coulometrically generated from reagent in a titration cell comprising the steps of:
flushing the titration cell with fresh reagent,
coulometrically titrating the fresh reagent to a predetermined endpoint level,
introducing a process sample to the titration cell,
coulometrically generating titrant in the titration cell to titrate the process sample,
determining the endpoint of the titration, and
measuring the coulombs of charge utilized to generate the titrant and relating it to the process sample concentration.

21. A method of automatic process titration as claimed in claim 20 wherein the flushing with reagent and introduction of process sample is obtained by controlling reagent and sample valves located in a cell loop connecting the valves and the titration cell.

22. A method of automatic process titration as claimed in claim 21 further including the step of circulating the titration cell contents through the cell loop during the titration.

23. A method of microprocessor control of automatic process titration in which the titrant is coulometrically generated from reagent in a titration cell comprising:
sending a signal from the microprocessor to a reagent valve driver causing it to operate a valve to flush the titration cell with fresh reagent,
sending a signal from the microprocessor to a current generator causing current to be applied to the titration cell to coulometrically titrate the fresh reagent to a predetermined endpoint,
sensing the endpoint in the titration cell,
sending a signal related to the sensed endpoint to the microprocessor,
comparing the sensed endpoint to a predetermined setpoint,
sending a signal from the microprocessor to the current generator, when the predetermined setpoint is reached, to cease current application,
sending a signal from the microprocessor to a sample valve driver causing it to operate a valve to introduce a process sample to the titration cell,
sending a signal from the microprocessor to the current generator causing current to be applied to the titration cell to coulometrically generate titrant from the reagent therein,
sensing the endpoint of the reaction between the titrant and the process sample in the titration cell,
sending a signal related to the sensed endpoint to the microprocessor,
comparing the sensed endpoint to the predetermined setpoint,
determining the coulombs of charge required to reach the setpoint,
relating the coulombs required to the concentration of the process sample, and
calculating the concentration.

24. A method of microprocessor control of automatic process titration as claimed in claim 23 further including repeating the sequence of steps and outputting the concentration calculated after each repetition as a trend signal updated after each repetition.

25. A method of microprocessor control of automatic process titration as claimed in claim 23 further including sending a signal from the microprocessor to an impeller motor driver after operating the sample valve driver to activate an impeller for circulating the titration cell contents for thorough mixing.

26. A method of microprocessor control of automatic process titration as claimed in claim 23 wherein the microprocessor receives function instructions from an operator controlled keyboard entry and provides visual output of titration operations on a display.

27. A method of microprocessor control of automatic process titration as claimed in claim 23 wherein the microprocessor is controlled by a stored program.

* * * * *